United States Patent
Hirota

(10) Patent No.: US 12,190,482 B2
(45) Date of Patent: Jan. 7, 2025

(54) ENDOSCOPE PROCESSOR, METHOD FOR OPERATING ENDOSCOPE PROCESSOR, AND STORAGE MEDIUM

(71) Applicant: OLYMPUS CORPORATION, Tokyo (JP)

(72) Inventor: Masashi Hirota, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 233 days.

(21) Appl. No.: 17/868,206

(22) Filed: Jul. 19, 2022

(65) Prior Publication Data

US 2022/0351350 A1    Nov. 3, 2022

Related U.S. Application Data

(63) Continuation of application No. PCT/JP2020/001891, filed on Jan. 21, 2020.

(51) Int. Cl.
*A61B 8/00*    (2006.01)
*A61B 1/00*    (2006.01)
(Continued)

(52) U.S. Cl.
CPC ............ *G06T 5/50* (2013.01); *A61B 1/00045* (2013.01); *A61B 1/0638* (2013.01); *G06T 5/00* (2013.01);
(Continued)

(58) Field of Classification Search
CPC ... G06T 5/50; G06T 5/00; G06T 2207/10024; G06T 2207/10069; G06T 2207/30101; A61B 1/0638; A61B 1/00045
See application file for complete search history.

(56) References Cited

U.S. PATENT DOCUMENTS

| 2010/0266202 A1 | 10/2010 | Minai |
|---|---|---|
| 2014/0221745 A1* | 8/2014 | Yamaguchi ............ H04N 23/69 600/109 |
| 2015/0245002 A1* | 8/2015 | Kuramoto .............. H05B 45/20 315/307 |

FOREIGN PATENT DOCUMENTS

| JP | 2012152284 A | 8/2012 |
|---|---|---|
| JP | 2014212925 A | 11/2014 |

(Continued)

OTHER PUBLICATIONS

International Search Report dated Mar. 10, 2020 issued in PCT/JP2020/001891.

*Primary Examiner* — Joel F Brutus
(74) *Attorney, Agent, or Firm* — Scully, Scott, Murphy & Presser, P.C.

(57) ABSTRACT

An endoscope processor comprises a processor. The processor causes a light source to generate, as illumination light, light in a first wavelength band in which hemoglobin absorption is smaller than that in a green band and light in a second wavelength band which is different from the first wavelength band. The processor causes an endoscope to image a return light so as to output an image signal. The processor acquires a first image obtained by the light in the first wavelength band from the image signal and detects unevenness information on mucosa from the first image. The processor acquires a second image obtained by the light in the second wavelength band from the image signal and synthesizes the unevenness information with the second image so as to generate a display image in which an uneven region in the second image is emphasized.

9 Claims, 8 Drawing Sheets

(51) Int. Cl.
*A61B 1/06* (2006.01)
*G06T 5/00* (2006.01)
*G06T 5/50* (2006.01)

(52) U.S. Cl.
CPC ............... *G06T 2207/10024* (2013.01); *G06T 2207/10068* (2013.01); *G06T 2207/30101* (2013.01)

(56) References Cited

FOREIGN PATENT DOCUMENTS

WO     2010050400   A1    5/2010
WO     2019130868   A1    7/2019

* cited by examiner

ENDOSCOPE PROCESSOR, METHOD FOR OPERATING ENDOSCOPE PROCESSOR, AND STORAGE MEDIUM

CROSS REFERENCE TO RELATED APPLICATION

This application is a continuation of International Patent Application No. PCT/JP2020/001891, having an international filing date of Jan. 21, 2020, which designated the United States, the entirety of which is incorporated herein by reference.

BACKGROUND

In an endoscope apparatus, a method of suppressing or emphasizing a specific part by image processing has been known to easily discover or diagnose the specific part. Japanese Unexamined Patent Application Publication No. 2014-212925 discloses a method of suppressing or emphasizing two different structures in a living body. Specifically, the method disclosed in Japanese Unexamined Patent Application Publication No. 2014-212925 performs two types of filtering processes with different wavelength bands on a violet narrow band light image so as to extract information of two types of structures, the gland duct and blood vessel, and thereby suppresses or emphasizes them.

SUMMARY

In accordance with one of some aspect, there is provided an endoscope processor comprising a processor, wherein
the processor
  causes a light source to generate, as illumination light, light in a first wavelength band in which hemoglobin absorption is smaller than that in a green band and light in a second wavelength band which is different from the first wavelength band;
  causes an endoscope to image a return light so as to output an image signal;
  acquires a first image obtained by the light in the first wavelength band from the image signal and detects unevenness information on mucosa from the first image; and
  acquires a second image obtained by the light in the second wavelength band from the image signal and synthesizes the unevenness information with the second image so as to generate a display image in which an uneven region in the second image is emphasized.

In accordance with one of some aspect, there is provided a method of operating an endoscope processor comprising:
  causing a light source to generate, as illumination light, light in a first wavelength band in which hemoglobin absorption is smaller than that in a green band and light in a second wavelength band which is different from the first wavelength band;
  causing an endoscope to image a return light so as to output an image signal;
  acquiring a first image obtained by the light in the first wavelength band from the image signal and detecting unevenness information on mucosa from the first image; and
  acquiring a second image obtained by the light in the second wavelength band from the image signal and synthesizing the unevenness information with the second image so as to generate a display image in which an uneven region in the second image is emphasized.

In accordance with one of some aspect, there is provided a storage medium storing a program for an endoscope processor, wherein
the program causes the processor to
  receive an image signal from a return light obtained when light in a first wavelength band in which hemoglobin absorption is smaller than that in a green band and light in a second wavelength band which is different from the first wavelength band are irradiated,
  acquire a first image obtained by the light in the first wavelength band from the image signal,
  detect unevenness information on mucosa from the first image,
  acquire a second image obtained by the light in the second wavelength band, and
  synthesize the unevenness information with the second image to generate a display image in which an uneven region in the second image is emphasized.

DESCRIPTION OF EXEMPLARY EMBODIMENTS

Figure 1:
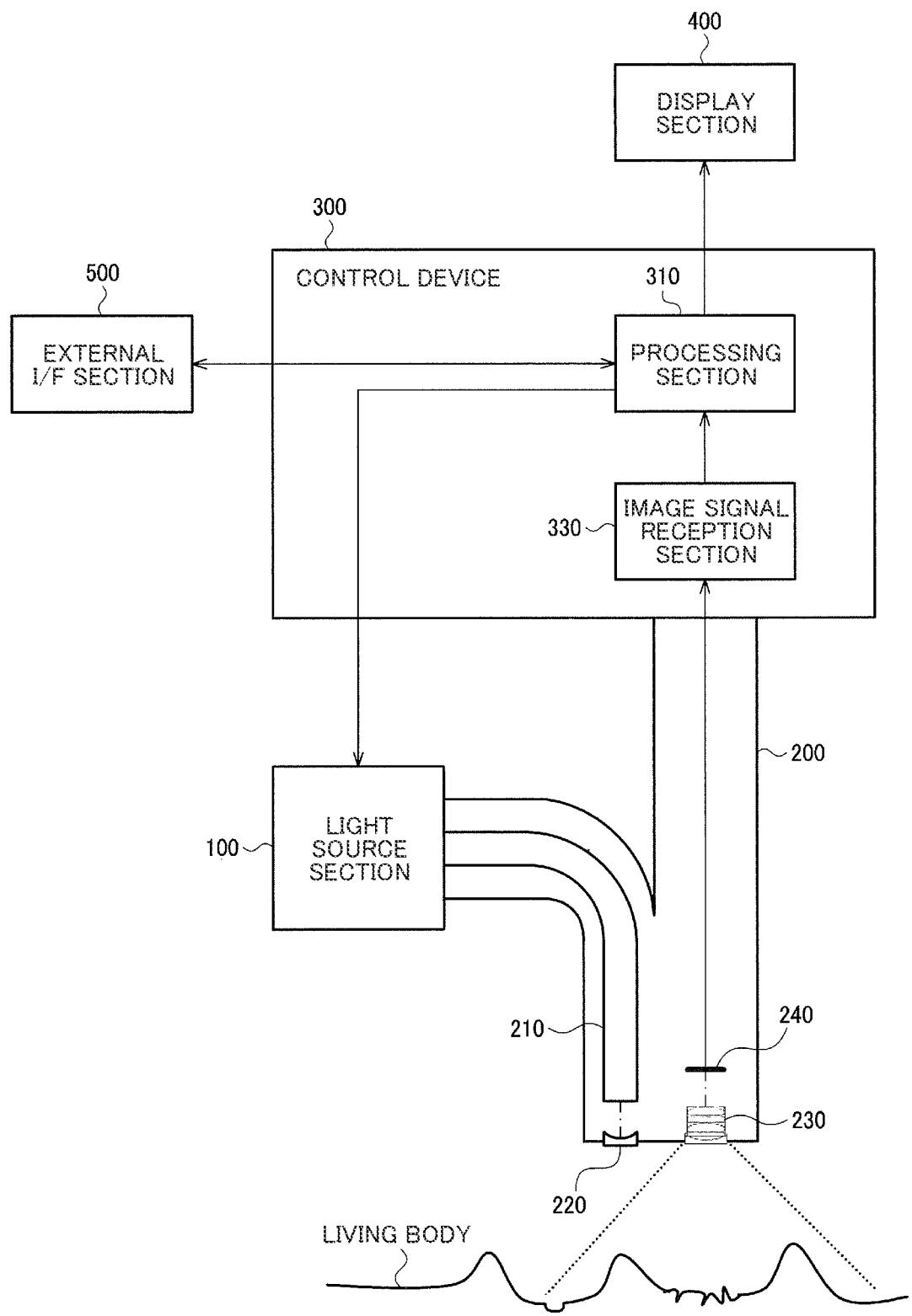
FIG. 1 illustrates a configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 illustrates a configuration example of an endoscope apparatus. The endoscope apparatus comprises an imaging section 200, a control device 300, a display section 400, an external I/F section 500 and a light source section 100. A flexible scope used in the urinary organ, the digestive tract or the like, and a rigid scope used for a laparoscope or the like can be assumed as the endoscope apparatus, for example. However, the endoscope apparatus is not limited thereto.

The light source section 100 is a device for generating illumination light. The light source section 100 is also referred to as a light source device. The light source section 100 generates white light and special light as illumination light. Specifically, the light source section 100 generates white light in a WLI (White Light Imaging) mode, and generates special light in a special light mode. The special light mode is, for example, an NBI (Narrow Band Imaging) mode generating violet narrow band light and green narrow band light as illumination light. The emission timing of illumination light may be either a simultaneous mode in which a plurality of light sources emits light at the same time, or a field sequential mode in which a plurality of light sources sequentially emit light.

The imaging section 200 is a part which is inserted into a living body and captures an image of a subject. The imaging section 200 is also referred to as a scope. The imaging section 200 includes a light guide 210, an illumination lens 220, an objective lens 230, and an imaging sensor 240. The imaging sensor 240 is also referred as an image sensor. The imaging section 200 has a connector, which is not shown. By the connector, the imaging section 200 is attached to/detached from the control device 300.

The light guide 210 guides illumination light emitted from the light source 100 to the distal end of the imaging section 200. The illumination lens 220 irradiates illumination light guided by the light guide 210 onto a subject. In the present embodiment, the subject is a living body. For example, in an endoscope apparatus for the urinary organ, the subject is mucosa of the bladder or the like. Alternatively, in an endoscope apparatus for the upper digestive tract, the subject is mucosa of the stomach, the esophagus or the like. Reflected light from the subject enters the objective lens 230. A subject image is formed by the objective lens 230, and the imaging sensor 240 captures the subject image.

The imaging sensor 240 images a return light from the subject onto which illumination light is irradiated so as to output an image signal. The imaging sensor 240 may either be a color image sensor in which color filters are provided for each pixel, or a monochromatic image sensor. The color image sensor is, for example, a Bayer color image sensor having color filters in a Bayer's arrangement, or a complementary color image sensor having a complementary color filter.

The imaging section 200 includes an A/D converter circuit. The A/D converter circuit converts an analog image signal from the imaging sensor 240 to a digital image signal. The A/D converter circuit is, for example, included in the imaging sensor 240.

The control device 300 performs signal processing including image processing. The control device 300 also controls each part of the endoscope apparatus. The control device 300 is also referred to as a processing device or a processor section. The control device 300 includes a processing section 310 and an image signal reception section 330. The processing section 310 is also referred to as a processing circuit or a processor.

The image signal reception section 330 receives an image signal from the imaging sensor 240. The image signal reception section 330 is, for example, a connector connecting the imaging section 200 and the control device 300, an interface circuit receiving the image signal, a preprocessing circuit generating image data from the image signal, or the like. The image signal reception section 330 and the processing section 310 may be implemented by separate hardware, or by integrated hardware.

The processing section 310 performs image processing based on the image signal received by the image signal reception section 330, and thereby generates a display image so as to output the display image to the display section 400. Moreover, the processing section 310 controls each part of the endoscope apparatus.

More specifically, the processing section 310 controls light emission timing of the light source and timing of capturing an image of the imaging sensor 240. For example, a user operates the external I/F section 500 to switch between the WLI mode and the special light mode. For example, when the special light mode is set, the processing section 310 instructs the light source section 100 to emit special light, generates a special light image from the image signal, and outputs the special light image to the display section 400. When the WLI mode is set, the processing section 310 instructs the light source section 100 to emit white light, generates a white light image from the image signal, and outputs the white light image to the display section 400.

The display section 400 is a device displaying a display image from the processing section 310. The display section 400 is, for example, a liquid crystal display device or the like. The external I/F section 500 is a device receiving operation of a user on the endoscope apparatus. The external I/F section 500 is, for example, a button, dial, pointing device, touch panel, foot switch, and the like.

2. Light Source Section

Hereinbelow, a case where a special light observation is the NBI observation will be described. However, the method of the present embodiment may also be applied to a special light observation other than NBI or white light observation. That is, when it is difficult to visually recognize the texture of the mucosa, or when the texture of the mucosa is to be emphasized, the method same as the present embodiment can be applied.

Figure 2:
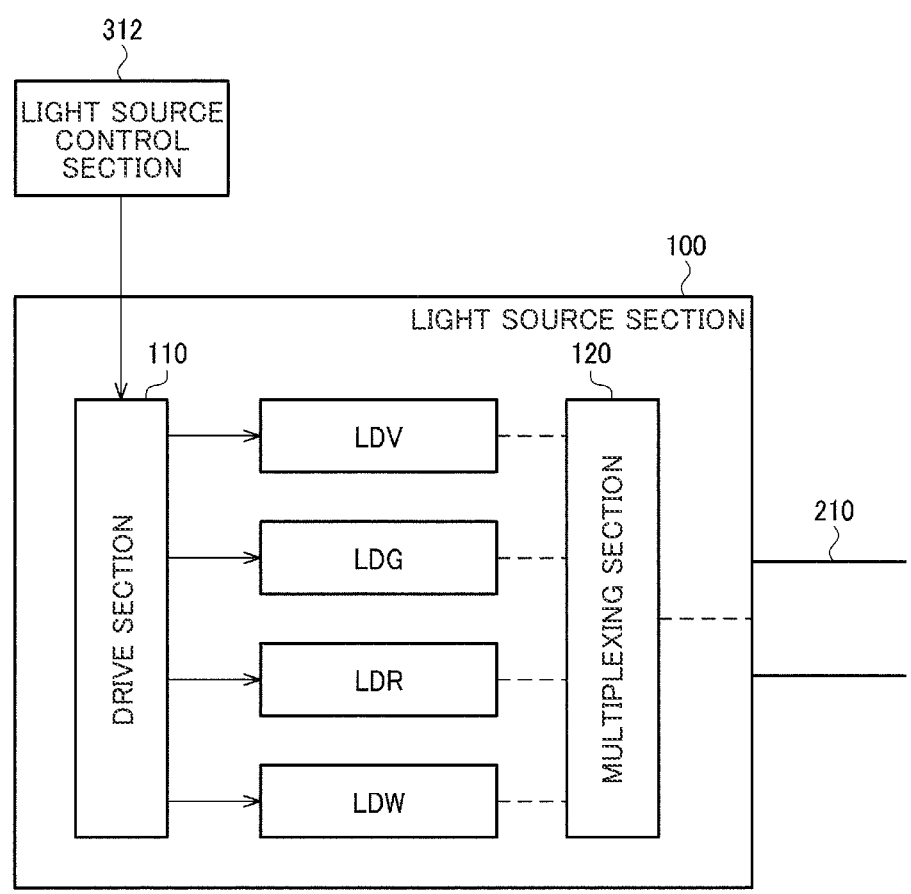
FIG. 2 illustrates a detail configuration example of a light source section.

FIG. 2 illustrates a detailed configuration example of the light source section 100. The light source section 100 includes a drive section 110, light sources LDV, LDG, LDR and LDW, and a multiplexing section 120.

A light source control section 312 inputs a control signal instructing the each light source about the light emission timing and light quantity to the drive section 110. As described later in FIG. 4, the light source control section 312 is included in the processing section 310. The drive section 110 drives the light sources LDV, LDG, LDR and LDW based on the control signal from the light source control section 312. For example, the drive section 110 supplies driving current to the light source, and thereby causes the light sources to emit light.

Each of the light sources LDV, LDG, LDR and LDW generates light having a predetermined wavelength characteristic. The light source LDR generates light in a first wavelength band, the light source LDV generates light in a second wavelength band, and the light source LDG generates light in a third wavelength band. The light in the second and third wavelength bands is narrow band light. The half-value width of narrow band light is, for example, several nm to several tens of nm. The light source LDW generates white light. The white light has a continuous spectrum in a visible light band. Alternatively, the white light may be composed of light in a plurality of bands. Each light source is, for example, LED or a laser. Alternatively, the white light source LDW may be a xenon lamp or the like. Further, the light sources LDV, LDG, and LDR may be implemented by a white light source and an optical filter through which each narrow band light passes.

A multiplexing section 120 multiplexes light emitted by the light sources LDV, LDG, LDR, and LDW, and make the multiplexed light incident to the light guide 210. The multiplexing section 120 is composed of, for example, a dichroic mirror and a lens. Alternatively, the multiplexing section 120 may be an optical fiber emitting light made incident from a plurality of incident ends to one emission end.

Figure 3:
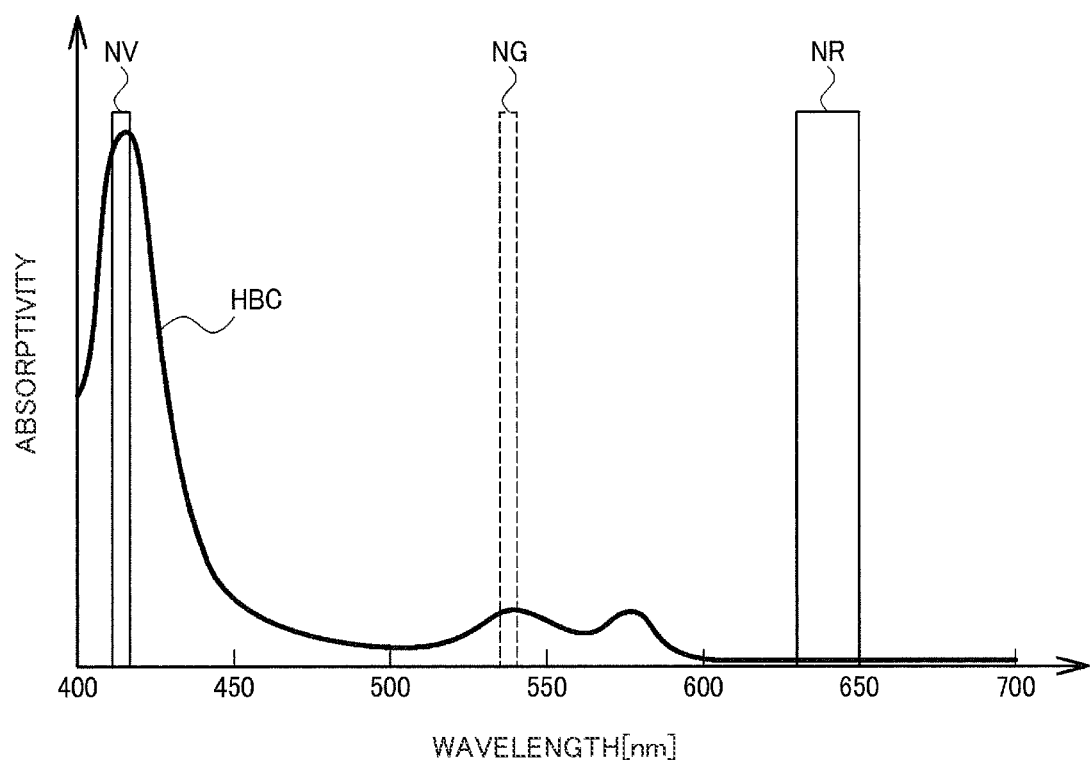
FIG. 3 illustrates an example of a wavelength characteristic of illumination light generated by the light source section.

FIG. 3 illustrates an example of a wavelength characteristic of illumination light generated by the light the source section 100. HBR is a wavelength characteristic of hemoglobin absorptivity.

The light source section 100 generates light in a plurality of wavelength bands as illumination light. The plurality of wavelength bands includes a wavelength band NR in which hemoglobin absorption is smaller than that in a green band. The NR is set as a first wavelength band. The green band corresponds to a green band when the visible light band is divided into three primary colors, and is, for example, 500 nm to 570 nm.

Specifically, the wavelength band NR belongs to a red band. The red band corresponds to a red band when the visible light band is divided into three primary colors, and is, for example, 570 nm to 700 nm. More specifically, the wavelength band NR belongs to a wavelength range in which the hemoglobin absorptivity is sufficiently small, and belongs to, for example, a wavelength range of 600 nm or more, and more desirably 630 nm or more. The wavelength band NR is, for example, 630 nm to 650 nm. Note that the width of the wavelength band NR is not limited to 20 nm, and may be several nm to one hundred and several tens of nm.

Further, the plurality of wavelength bands of illumination light includes a wavelength band NV. The NV is set as a second wavelength band. The wavelength band NV belongs to a violet band, and light of the wavelength band NV is violet narrow band light used in NBI (Narrow Band Imaging). The violet band is, for example, 400 nm to 430 nm.

Specifically, the peak wavelength of the wavelength band NV is 415 nm, which corresponds to the maximum in the absorptivity HBC. The wavelength band NV is a narrow band, and its width is, for example, several nm to several tens of nm. Note that the peak wavelength in the wavelength band NV may be in the predetermined wavelength range in the absorptivity HBC including the maximum, and in a range of, for example, 400 nm to 430 nm.

Further, the plurality of wavelength bands of illumination light includes a wavelength band NG. The NG is set as a third wavelength band. Light of the wavelength band NG is green narrow band light used in NBI.

Specifically, the peak wavelength of the wavelength band NG is 540 nm. The wavelength band NG is a narrow band, and its width is, for example, several nm to several tens of nm. Note that the peak wavelength of the wavelength band NG may belong to a green band, and for example, in a range of 530 nm to 550 nm.

The ratio of quantity of light in the wavelength bands NV and NG may be optional. For example, the ratio of quantity of light in the wavelength bands NV and NG is set to be a ratio of quantity of light appropriate for NBI. The ratio of quantity of light in the wavelength bands NV and NG, and the ratio of quantity of light in the wavelength bands NG and NR may also be optional. These ratios of quantity of light may be set to a ratio of quantity of light appropriate for texture emphasis described later.

In the above, NBI and light in the wavelength band NR are combined, but without being limited to this, white light and light in the wavelength band NR may be combined. Further, in the above, light of 630 nm to 650 nm is used as light in the wavelength band NR, but without being limited to this. For example, in a case where white light is generated in LED of RGB, the red light may be used as light in the wavelength band NR.

For example, in an endoscope observation using NBI (Narrow Band Imaging), there is a problem that it is difficult to know the texture of the mucosa including uneven information although a flat lesion can be easily found as compared with an endoscope observation using normal light. The texture is an indicator for judging whether a lesion is cancer or not, and thus is an important piece of information for lesion diagnosis.

As a result, in some embodiments described above, the light source section 100 generates light in a plurality of wavelength bands including the wavelength band NR, in which the hemoglobin absorption is smaller than that in the green band. In the wavelength band NR, the hemoglobin absorption is small, and therefore, information of the blood vessel is suppressed and information of the texture is relatively large in an image captured by light in the wavelength band NR. That is, the texture information can be acquired separately from the blood vessel information. Then, by using the texture information, it becomes possible to improve visibility of the texture in an endoscopic image.

For example, blood vessels of the superficial layer of the mucosa can be observed in high contrast in NBI, but it tends to be difficult to visually recognize the texture of the mucosa as compared with the white light observation. Although the texture of the mucosa was confirmed by switching between the white light observation and NBI conventionally, in the present embodiment, it becomes possible to emphasize the texture of the mucosa in an NBI image. As described later, also in the white light observation, it is possible to emphasize the texture of the mucosa by using light in the wavelength band NR.

In the above-described Japanese Unexamined Patent Application Publication No. 2014-212925, structural information of the gland duct and blood vessels is extracted from a violet narrow band light image. However, the violet narrow band light image is not suited as an object for extracting the texture information. More specifically, in the violet narrow band light image, absorption change by the blood vessels is large so that superficial blood vessels generated by angiogenesis or the like are highly contrasted in a site of lesion, and therefore, the texture information is easily hidden. Moreover, in the violet narrow band light image, uneven structure relating to the texture and blood vessels are not always in different wavelength bands. Therefore, when the texture information is extracted, the blood vessel information may be included.

In the following, details of a method for emphasizing the texture will be described along with operation explanation of the processing section 310.

3. First Embodiment

Figure 4:
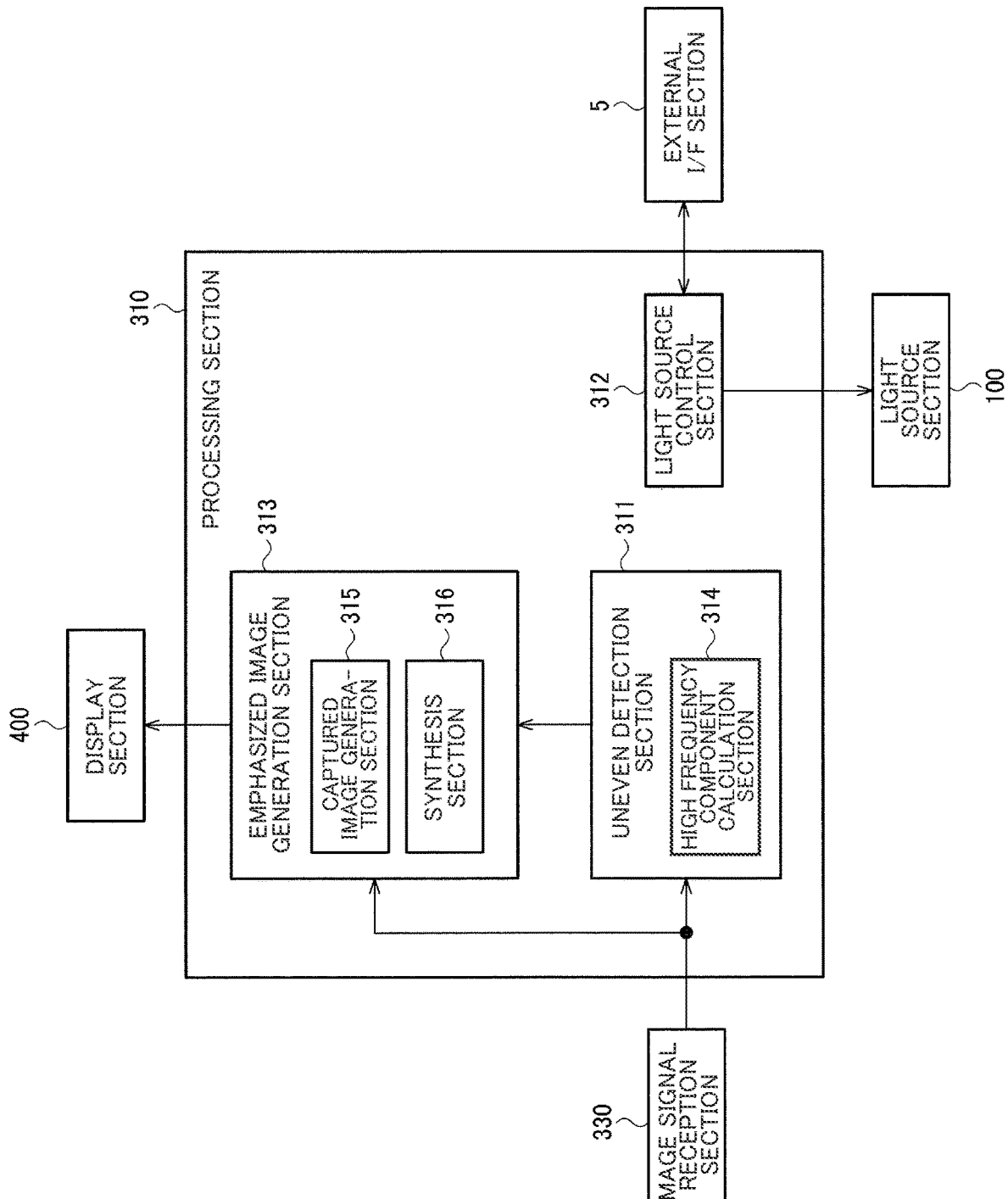
FIG. 4 illustrates a configuration example of a processing section in accordance with a first embodiment.

FIG. 4 illustrates a configuration example of the processing section 310 in accordance with a first embodiment. The processing section 310 includes an uneven detection section 311, the light source control section 312, and an emphasized image generation section 313. Hereinbelow, although a case where the bladder is the subject is described as an example, the subject may be other organs or tissues.

The light source control section 312 controls the emission timing and the quantity of light of the light sources LDV, LDG, LDR, and LDW included in the light source section 100.

Specifically, when a user sets the WLI mode via the external I/F section 500, the light source control section 312 causes the light source LDW to emit light based on a mode setting signal from the external I/F section 500. Further, when the user sets the NBI mode via the external I/F section 500, the light source control section 312 causes the light sources LDV, LDG, and LDR to emit light based on the mode setting signal from the external I/F section 500. In the first embodiment, the NBI mode is set.

The uneven detection section 311 acquires a first image obtained by the light in the wavelength band NR from an image signal so as to detect unevenness information of the mucosa from the first image. The emphasized image generation section 313 produces a display image by emphasizing an unevenness of the mucosa based on the unevenness information in a captured image obtained by the image signal.

As such, since the hemoglobin absorption is small in the wavelength band NR, in the first image obtained by the light in the wavelength band NR, the blood vessel information is suppressed, and the texture information relatively becomes large. Then, by detecting the unevenness information of the mucosa from the first image, the unevenness of the mucosa can be emphasized in a captured image obtained by NBI. Herewith, in the NBI observation, observation of superficial blood vessels of the mucosa and observation of the texture of the mucosa may be both attained. Further, in the first image, the texture information can be obtained separately from the blood vessel information, so that even when the wavelength bands of the blood vessel and texture overlap in an image, only the texture can be appropriately emphasized.

Herein, the first image is produced from a signal corresponding to the wavelength band NR among image signals. Specifically, when a Bayer color image sensor is used, the wavelength band NR is imaged by R pixels. In this case, the uneven detection section 311 acquires the first image from an R signal of the image signal. Alternatively, in a field sequential mode using a monochromatic image sensor, the uneven detection section 311 acquires the first image from image signals when the light source LDR emits light.

The unevenness information of the mucosa is information corresponding to the unevenness of the mucosa among information included in the first image, and affects visual texture. For example, it is the one in which broad shape information is removed rather than the desired unevenness. The broad shape information is a roll or a fold of the entire mucosa rather than a fine structure on the surface of the mucosa. More specifically, the unevenness of the mucosa is a fine structure generated on the surface of the mucosa accompanied with development of a lesion. For example, cancer developed in the mucosa of the bladder causes fine peeling on mucosa cells, and unevenness due to the peeling affects the texture of the mucosa.

As shown in FIG. 4, the uneven detection section 311 includes a high frequency component calculation section 314. Further, the emphasized image generation section 313 includes a captured image generation section 315 and a synthesis section 316. In the following, the procedure of the image processing in accordance with the first embodiment is described with reference to FIG. 5.

As described in FIG. 3, the wavelength band NR for acquiring the first image belongs to the red band. That is, in FIG. 5, an R image IMR corresponds to the first image. The high frequency component calculation section 314 calculates the high frequency component from the R image IMR so as to detect the unevenness information IMTX.

Specifically, the frequency component calculation section 314 performs a high-pass filtering process or a band-pass filtering process on the R image IMR to calculate the high frequency component. The high frequency component is calculated for each pixel in the R image IMR. A passband of the high-pass filtering process or the band-pass filtering process is set to include frequency bands of uneven information relating to the desired texture. The passband may include a wavelength band of superficial blood vessels of the mucosa.

The return light from the subject includes light reflected at a surface of the subject and light scattered inside the subject. In the red band, the hemoglobin absorptivity is smaller than in the green band. Since such light in the red band is hardly absorbed by blood vessels inside the subject, the R image IMR includes a relatively large amount of unevenness information on the surface of the subject. In the present embodiment, the texture of the mucosa can be emphasized by using this unevenness information. A method for detecting the unevenness information by the uneven detection section 311 is not limited to a method for calculating the high frequency component from the R image IMR as described above. For example, the uneven detection section 311 may detect the unevenness information of the surface of the mucosa by a known morphological processing or the like.

The captured image generation section 315 generates a captured image using a plurality of images obtained by light in a plurality of wavelength bands. The synthesis section 316 synthesizes the unevenness information IMTX with a V image IMV included in a plurality of images so as to emphasize unevenness.

More specifically, the captured image generation section 315 generates the V image IMV and a G image IMG as captured images. The V image IMV is a second image obtained by light in the wavelength band NV, and the G image IMG is a third image obtained by light in the wavelength band NG. The captured image is also referred to as a base image, which is a base for the emphasis processing. The synthesis section 316 adds the unevenness information IMTX to the V image IMV in each pixel at a predetermined ratio so as to generate an emphasized V image IMVTX.

As such, unevenness in the V image IMV may be emphasized by synthesizing the unevenness information IMTX with the V image IMV, which is different from the R image IMR. Then, by generating a captured image using a plurality of images including the V image IMV, a display image in which the texture is emphasized can be obtained.

In the above, the V image IMV is set as the second image, but the second image may be an image obtained by light in the second wavelength band other than the wavelength band NV. As described later, in the texture emphasis in the white light observation, the second image is a G image in a white light image.

The synthesis section 316 inputs the emphasized V image IMVTX to a G channel and a B channel of the display image. Further, the synthesis section 316 inputs the G image IMG to an R channel of the display image.

As such, unevenness in the V image input to the G channel of the display image is emphasized. The G channel has large contribution to brightness, so that unevenness in the brightness is emphasized. Accordingly, the texture of the mucosa can be efficiently emphasized. Further, an NBI image can be composed by inputting the V image to the G and B channels, and inputting the G image to the R channel. That is, according to the first embodiment, visibility of the texture of the mucosa can be improved in the NBI image.

Figure 5:
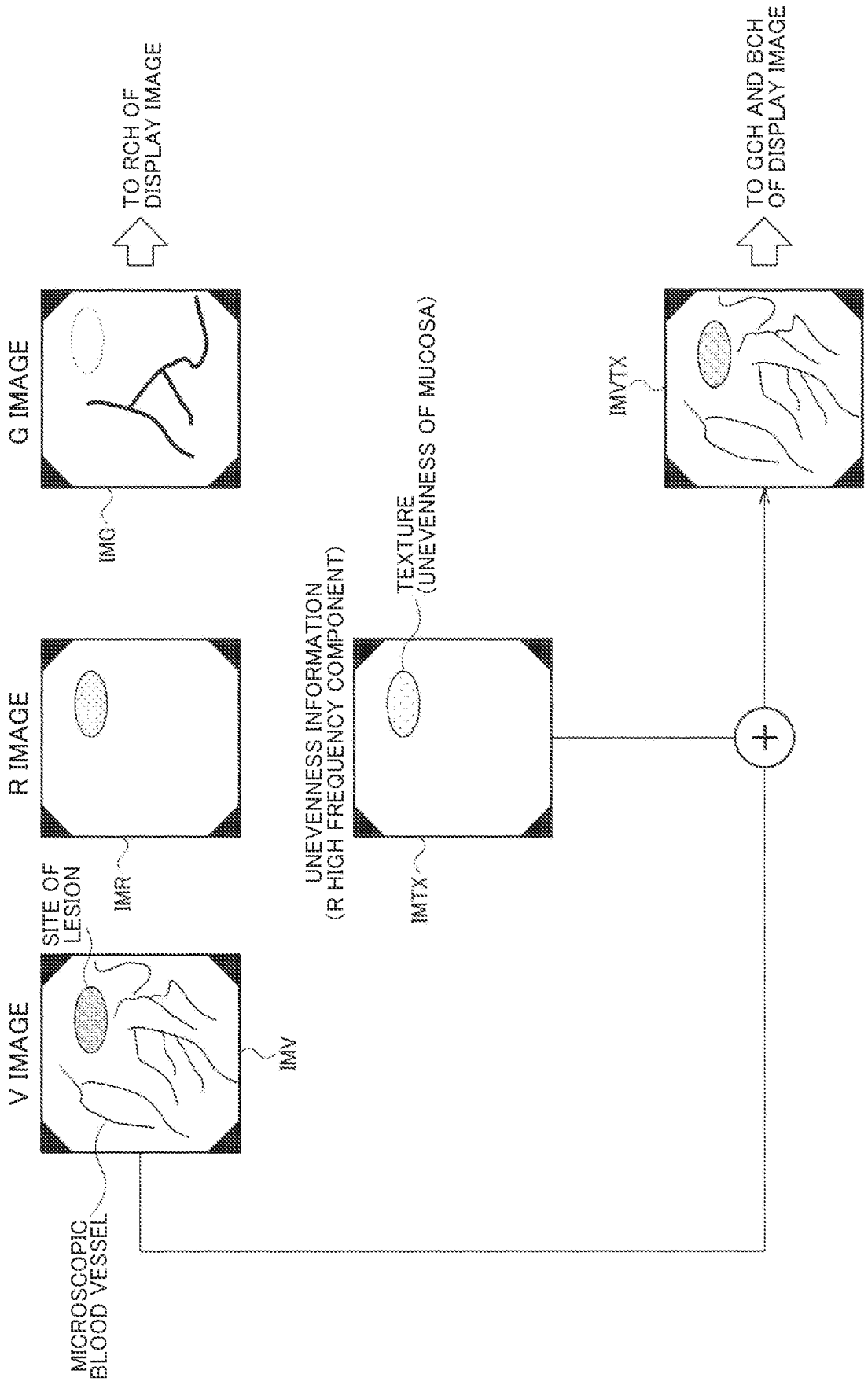
FIG. 5 illustrates a procedure of an image processing in accordance with the first embodiment.

A site of lesion shown in FIG. 5 is, for example, cancer developed in the bladder mucosa. In cancer developed in the bladder mucosa, superficial blood vessels are closely gathered, and therefore, it appears as a region with a different color or brightness than the surrounding normal mucosa in an NBI image. In this region of cancer, since absorption of violet narrow band light is large, a signal value of the G channel that is a brightness component in a display image becomes small. Therefore, it is difficult to visually recognize the texture of the mucosa. According to the first embodiment, unevenness information is synthesized with the V image, i.e., the G channel of the display image, so that the texture of the mucosa can be easily visually recognized. Accordingly, in the bladder observation by NBI, visibility of a lesion by hemoglobin absorption and visibility of a lesion by the texture can be both attained.

4. Second Embodiment

Figure 6:
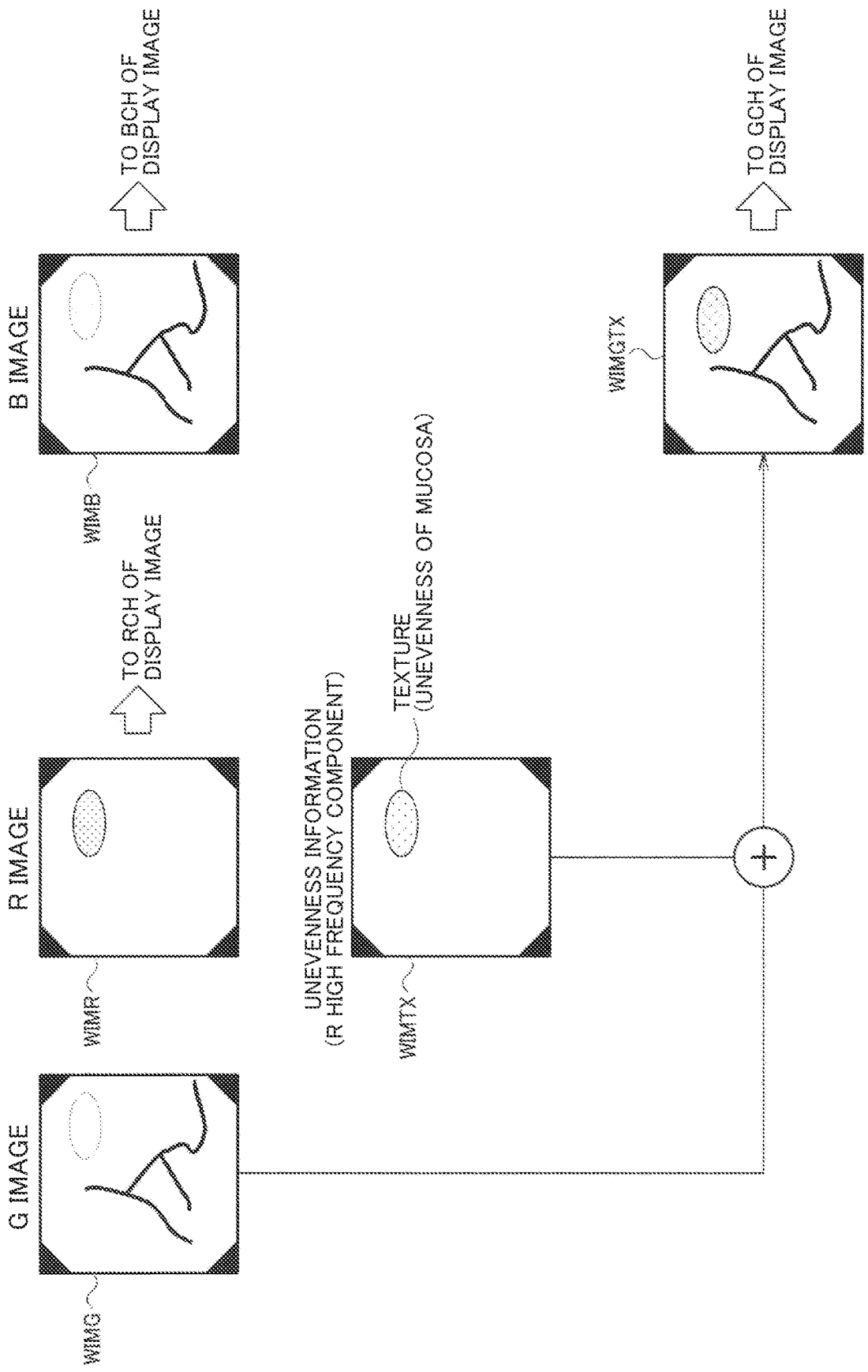
FIG. 6 illustrates a procedure of an image processing in accordance with a second embodiment.

FIG. 6 illustrates a procedure of the image processing in accordance with a second embodiment. Configuration of the processing section 310 in the second embodiment is same as that shown in FIG. 4 according to the first embodiment.

In the second embodiment, illumination light is white light. That is, the light source control section 312 causes the light source LDW to emit light. Further, in the second embodiment, a red band, a green band, and a blue band in the white light is respectively a first wavelength band, second wavelength band, and a third wavelength band.

The captured image generation section 315 generates a white light image from an image signal. More specifically, the captured image generation section 315 generates an R image WIMR from an R channel of the image signal, a G image WIMG from a G channel of the image signal, and a B image WIMB from a B channel of the image signal. The R image WIMR is a first image of the red band, the G image WIMG is a second image of the green band, and the B image WIMB is a third image of the blue band.

The uneven detection section 311 detects unevenness information WIMTX from an R channel of the captured image that is a white light image.

Specifically, the high frequency component calculation section 314 calculates a high frequency component from the R image WIMR so as to detect the unevenness information WIMTX. The high frequency component calculation section 314 performs the high-pass filtering process or the band-pass filtering process on the R image WIMR to calculate the high frequency component. The high frequency component is calculated for each pixel in the R image WIMR. The passband of the high-pass filtering process or the band-pass filtering process is set to include frequency bands of uneven information relating to the desired texture. The passband may include a wavelength band of superficial blood vessels of the mucosa.

The synthesis section 316 emphasizes unevenness by synthesizing the unevenness information WIMTX with a G channel of the captured image.

Specifically, the synthesis section 316 adds the unevenness information WIMTX to the G image WIMG in each pixel at a predetermined ratio so as to generate an emphasized G image WIMGTX. The synthesis section 316 inputs the emphasized G image WIMGTX to the G channel of the display image. Further, the synthesis section 316 inputs the R image WIMR to the R channel of the display image, and inputs the B image WIMB to the B channel of the display image.

According to the second embodiment, visibility of the texture of the mucosa can be improved in the white light observation. As described above, since the hemoglobin absorptivity is smaller in the red band than in the green band, light in the red band is hardly absorbed within the subject. Therefore, The R image WIMR in the white light image includes a relatively large amount of unevenness information on a surface of the subject. In the present embodiment, the texture of the mucosa can be emphasized by using this unevenness information.

Further, according to the second embodiment, unevenness of the G image WIMG input to the G channel of the display image is emphasized. Unevenness in the brightness is thereby emphasized, so that the texture of the mucosa can be efficiently emphasized.

A site of lesion shown in FIG. 6 is, as with FIG. 5, cancer developed in the bladder mucosa. In the white light observation, visibility of the texture of the mucosa is higher than the NBI observation in cancer developed in the bladder mucosa. However, in the G channel that is a brightness component, the hemoglobin absorption is large, so that the texture information of the mucosa may possibly be relatively suppressed. According to the second embodiment, the texture of the G channel can be emphasized by using unevenness information in the R channel, in which the hemoglobin absorption is small. Thus, visibility of the texture of the mucosa can be further improved in the white light observation.

5. Third Embodiment

Figure 7:
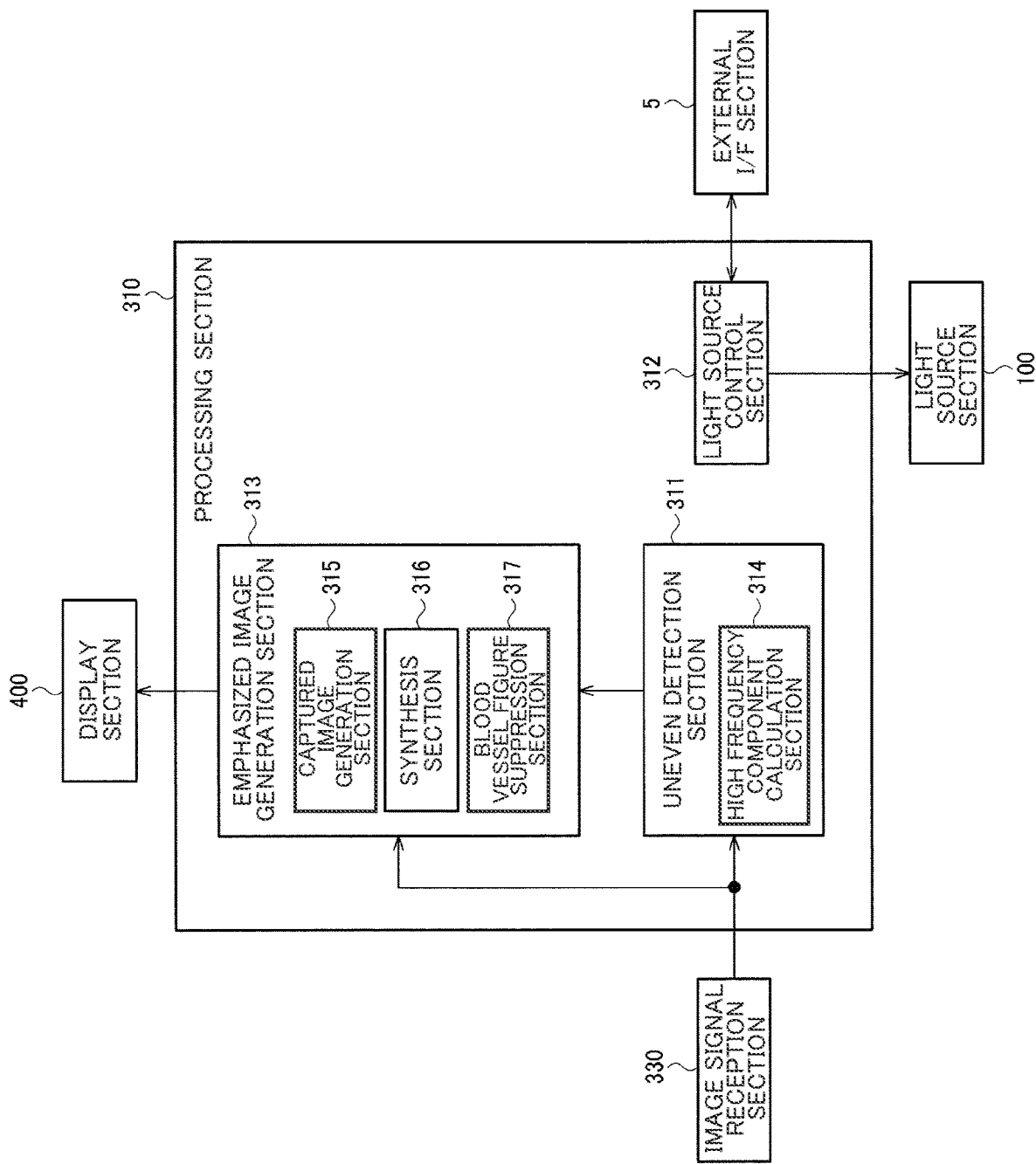
FIG. 7 illustrates a configuration example of the processing section in accordance with a third embodiment.

FIG. 7 illustrates a configuration example of the processing section 310 in accordance with a third embodiment. In the third embodiment, the emphasized image generation section 313 further includes a blood vessel figure suppression section 317. In the following, a part different from the first embodiment is mainly described, and description of the part same as the first embodiment is appropriately omitted.

Figure 8:
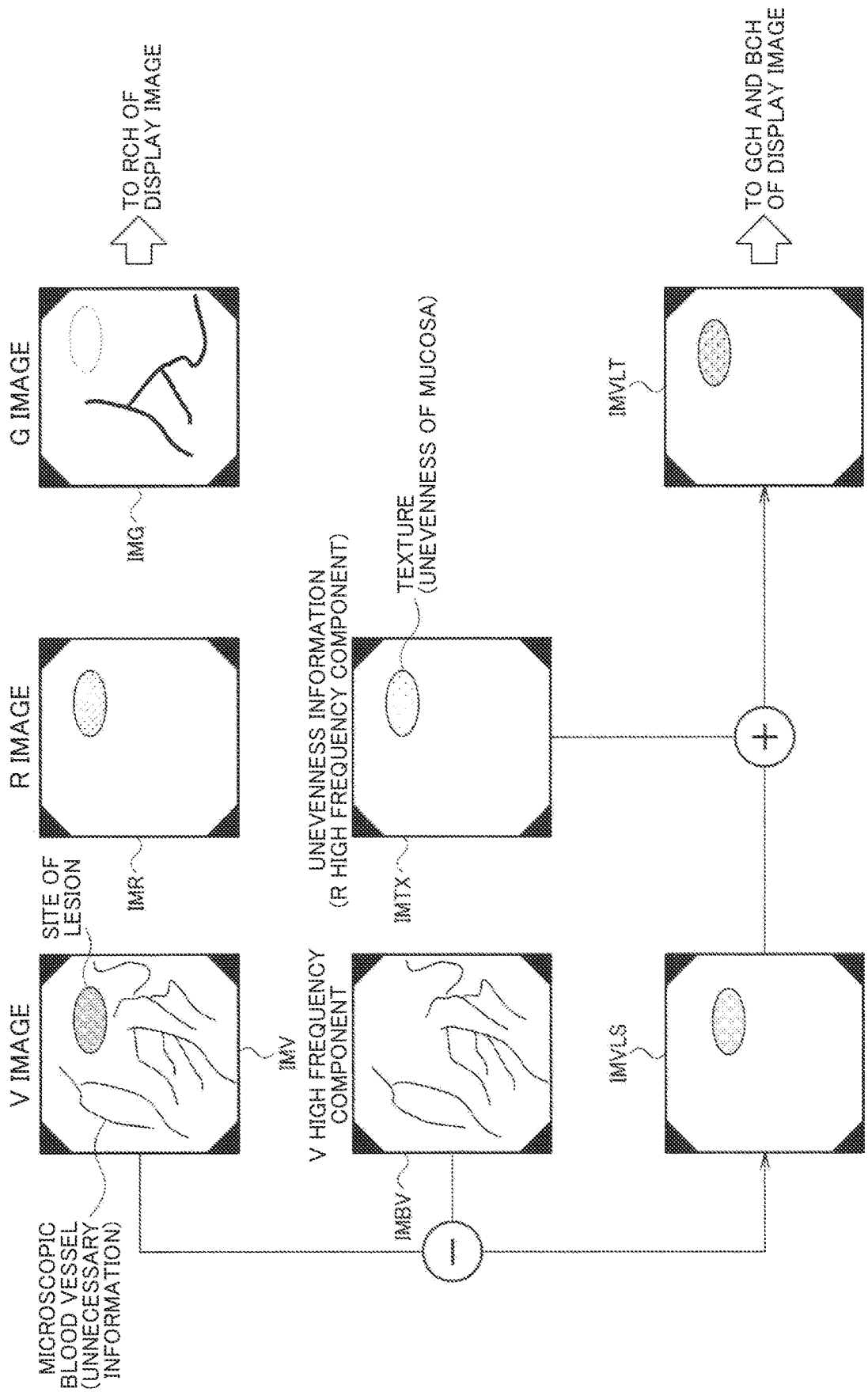
FIG. 8 illustrates a procedure of an image processing in accordance with the third embodiment.

FIG. 8 illustrates a procedure of image processing in accordance with the third embodiment. In the third embodiment, the NBI mode is set. That is, the light source control section 312 causes the light sources LDV, LDG, and LDR to emit light, and thereby generates violet narrow band light, green narrow band light, and red narrow band light.

The blood vessel figure suppression section 317 suppresses contrast of a blood vessel figure in a captured image. Specifically, the blood vessel figure suppression section 317 calculates a high frequency component of a V image IMV including a blood vessel figure, subtracts the high frequency component from the V image IMV to suppress the contrast of the blood vessel figure. The V image after suppressing the contrast of the blood vessel figure is referred to as IMVLS.

Specifically, the blood vessel figure suppression section 317 performs the high-pass filtering process or the band-pass filtering process on the V image IMV to calculate the high frequency component. The high frequency component is calculated for each pixel in the V image IMV. The passband of the high-pass filtering process or the band-pass filtering process is set to include frequency bands of superficial blood vessels of the mucosa.

The synthesis section 316 adds the V image IMVLS after suppressing the contrast of the blood vessel figure and unevenness information IMTX extracted from the R image IMR so as to output an image IMVLT in which the texture has been emphasized. The synthesis section 316 inputs IMVLT in which the texture has been emphasized to the G channel and B channel of the display image, and inputs a G image IMG to the R channel of the display image.

As described above, cancer developed in the mucosa of the bladder appears as a region with a different color or brightness than the surrounding normal mucosa in the NBI image. On the other hand, in normal mucosa, superficial blood vessels are present in a lower density as compared to cancer, and each blood vessel is separated. Accordingly, extraction of a high frequency component from the V image IMV enables extraction of information of superficial blood vessels in normal mucosa. Subtraction of this information of superficial blood vessels from the V image IMV enables to suppress superficial blood vessels in normal mucosa while leaving the region of cancer in the V image IMV. Since microscopic blood vessels which are unnecessary information in NBI observation of the bladder can be thereby suppressed, the visibility of the texture of the mucosa in a site of lesion can be further improved.

The control device 300 including the processing section 310 may be configured as follows. That is, the control device 300 includes a memory storing information, and a processor which operates based on the information stored in the memory. For example, the information is a program and various data. The processor includes hardware.

The processor causes the light source section 100 to generate, as illumination light, light in a plurality of wavelength bands including the first wavelength band in which the hemoglobin absorption is smaller than that in the green band. The processor receives an image signal from the imaging section 200 that images a return light from a living body onto which illumination light is irradiated. The processor acquires a first image obtained by the light in the first wavelength band from the image signal so as to detect unevenness information of the mucosa from the first image. Then, the processor emphasizes the unevenness of the mucosa based on the unevenness information in a captured image obtained by the image signal so as to generate a display image.

For example, the processor may have functions of its sections each implemented by individual hardware, or may have the functions of its sections each implemented by integrated hardware. For example, the processor includes hardware, and the hardware may include at least one of a circuit that processes a digital signal and a circuit that processes an analog signal. For example, the processor may be configured with one or more circuit devices mounted on a circuit board, or one or more circuit elements. The one or more circuit devices are, for example, an integrated circuit (IC). The one or more circuit elements are, for example, a resistor or a capacitor. The processor may be a central processing unit (CPU), for example. Note that the processor is not limited to the CPU, and various other processors such as a graphics processing unit (GPU) and a digital signal processor (DSP) may also be used. Alternatively, the processor may be an integrated circuit device such as an application specific integrated circuit (ASIC) and a field-programmable gate array (FPGA). The processor may include an amplifier circuit, a filter circuit or the like that processes an analog signal.

The memory may be a semiconductor memory such as SRAM or DRAM, a register, a magnetic storage device such as a hard disk drive, or may be an optical storage device such as an optical disc device. For example, the memory stores computer-readable instructions. When the instructions are executed by the processor, the functions of the processing section 310 are implemented as processes. The instruction described herein may be an instruction set that constitutes a program, or may be an instruction that instructs the hardware circuit in the processor to operate.

The program achieving the process executed by the processing section 310 can be stored in, for example, a non-transitory information storage medium, which is a computer-readable medium. The information storage medium can be accomplished by, for example, an optical disk, a memory card, an HDD, or a semiconductor memory (ROM). The semiconductor memory is, for example, an ROM. The processing section 310 executes various processes of the present embodiment based on the program and data stored in the information storage medium. That is, the information storage medium stores a program for causing a computer to function as the processing section 310. The computer is a device comprising an input device, a processing section, a storage section, and an output section.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope processor comprising:
   a processor comprising hardware, wherein the processor is configured to:
   cause a light source to generate, as illumination light, light in a first wavelength band belonging to a red wavelength band and light in a second wavelength band different from the first wavelength band;
   cause an endoscope to image a return light from a subject illuminated by the illumination light so as to output an image signal;
   acquire a first image obtained by the light in the first wavelength band from the image signal and detect unevenness information on mucosa from the first image;
   acquire a second image obtained by the light in the second wavelength band from the image signal and synthesize the unevenness information with the second image so as to generate an emphasized second image in which an uneven region in the second image is emphasized; and input the emphasized second image to a G channel of a display image.

2. The endoscope processor as defined in claim 1, wherein the processor is configured to calculate a high frequency component from the first image so as to detect the unevenness information.

3. The endoscope processor as defined in claim 1, wherein the processor is configured to suppress contrast of a blood vessel figure in the second image.

4. The endoscope processor as defined in claim 3, wherein the processor is configured to:

calculate a high frequency component of the second image including the blood vessel figure; and subtract the high frequency component from the second image so as to suppress the contrast of the blood vessel figure.

5. The endoscope processor as defined in claim 1, wherein the second wavelength band includes a violet wavelength band.

6. The endoscope processor as defined in claim 5, wherein the illumination light comprises light in a third wavelength band including a green wavelength band, and wherein the processor is configured to:

calculate a high frequency component from the first image so as to detect the unevenness information;

synthesize the unevenness information with the second image so as to generate the emphasized second image in which the uneven region in the second image is emphasized; and input the emphasized second image to a B channel and the G channel of the display image, and input a third image obtained by the light in the third wavelength band to an R channel of the display image.

7. The endoscope processor as defined in claim 1, wherein the illumination light is white light, wherein the first wavelength band is the red wavelength band in the white light, wherein the second wavelength band includes a green wavelength band and a blue wavelength band in the white light, and wherein the processor is configured to detect the unevenness information from the first image being an R channel in a white light image obtained by the white light and synthesize the unevenness information with the second image being a G channel in the white light image so as to emphasize the uneven region.

8. A method comprising:

causing a light source to generate, as illumination light, light in a first wavelength band belonging to a red wavelength band and light in a second wavelength band different from the first wavelength band;

causing an endoscope to image a return light from a subject illuminated by the illumination light so as to output an image signal;

acquiring a first image obtained by the light in the first wavelength band from the image signal and detecting unevenness information on mucosa from the first image;

acquiring a second image obtained by the light in the second wavelength band from the image signal and synthesizing the unevenness information with the second image so as to generate an emphasized second image in which an uneven region in the second image is emphasized; and inputting the emphasized second image to a G channel of a display image.

9. A non-statutory computer-readable storage medium storing a program for an endoscope processor, wherein the program causes the endoscope processor to at least:

cause a light source to generate, as illumination light, light in a first wavelength band belonging to a red wavelength band and light in a second wavelength band different from the first wavelength band;

cause an endoscope to image a return light from a subject illuminated by the illumination light so as to output an image signal;

acquire a first image obtained by the light in the first wavelength band from the image signal, and detect unevenness information on mucosa from the first image, acquire a second image obtained by the light in the second wavelength band, and synthesize the unevenness information with the second image to generate an emphasized second image in which an uneven region in the second image is emphasized; and input the emphasized second image to a G channel of a display image.

* * * * *